(12) United States Patent
Klausmeyer

(10) Patent No.: US 7,112,709 B2
(45) Date of Patent: Sep. 26, 2006

(54) METHOD FOR REUSING HEAVY END BY-PRODUCTS IN THE MANUFACTURE OF POLYCHLORINATED ALKANES

(75) Inventor: Rodney L. Klausmeyer, Wichita, KS (US)

(73) Assignee: Vulcan Chemicals, Birmingham, AL (US)

( * ) Notice: Subject to any disclaimer, the term of this patent is extended or adjusted under 35 U.S.C. 154(b) by 548 days.

(21) Appl. No.: 10/657,895

(22) Filed: Sep. 9, 2003

(65) Prior Publication Data

US 2005/0054887 A1 Mar. 10, 2005

(51) Int. Cl.
*C07C 17/02* (2006.01)
*C07C 17/04* (2006.01)
*C07C 17/093* (2006.01)
*C07C 17/35* (2006.01)

(52) U.S. Cl. .................. 570/216; 570/231; 570/234; 570/238; 570/246; 570/251; 570/252; 570/255; 570/261; 570/262

(58) Field of Classification Search ................ 570/216, 570/231, 234, 238, 246, 251, 252, 255, 261, 570/262

See application file for complete search history.

(56) References Cited

U.S. PATENT DOCUMENTS

| 2,442,323 A | 5/1948 | Davis et al. ................. 260/654 |
| 2,442,324 A | 5/1948 | Heitz et al. .................. 260/654 |
| 2,577,388 A | 12/1951 | Warren ....................... 260/654 |
| 2,727,076 A | 12/1955 | Warren ....................... 260/658 |
| 2,857,438 A | 10/1958 | Obrecht et al. ............. 260/654 |
| 5,426,256 A | 6/1995 | Petrosky ..................... 570/234 |
| 5,792,893 A | 8/1998 | Wilson et al. .............. 570/257 |
| 6,313,360 B1 | 11/2001 | Wilson et al. .............. 570/257 |

*Primary Examiner*—Elvis O. Price
(74) *Attorney, Agent, or Firm*—Armstrong, Kratz, Quintos, Hanson & Brooks, LLP

(57) ABSTRACT

A method for recovering much of the carbon and chlorine value in the heavy ends and other undesired by-products formed during the production of a $C_3$ or higher polychlorinated alkane through the reaction of carbon tetrachloride with an olefine or chlorinated olefine, the improvement comprising the step of first separating the heavy ends and any other higher or lower boiling chlorohydrocarbon impurities from most of the desired product, and subjecting the separated heavy ends and impurities therewith to a high temperature exhaustive chlorination to produce carbon tetrachloride, tetrachloroethene, and minor amounts of hexachlorobutadiene and hexachlorobenzene by-products.

16 Claims, 2 Drawing Sheets

1,1,1,3,3,3-HEXACHLOROPROPANE PROCESS 1,1,1,3,3-PENTACHLOROPROPANE PROCESS

Figure 1:
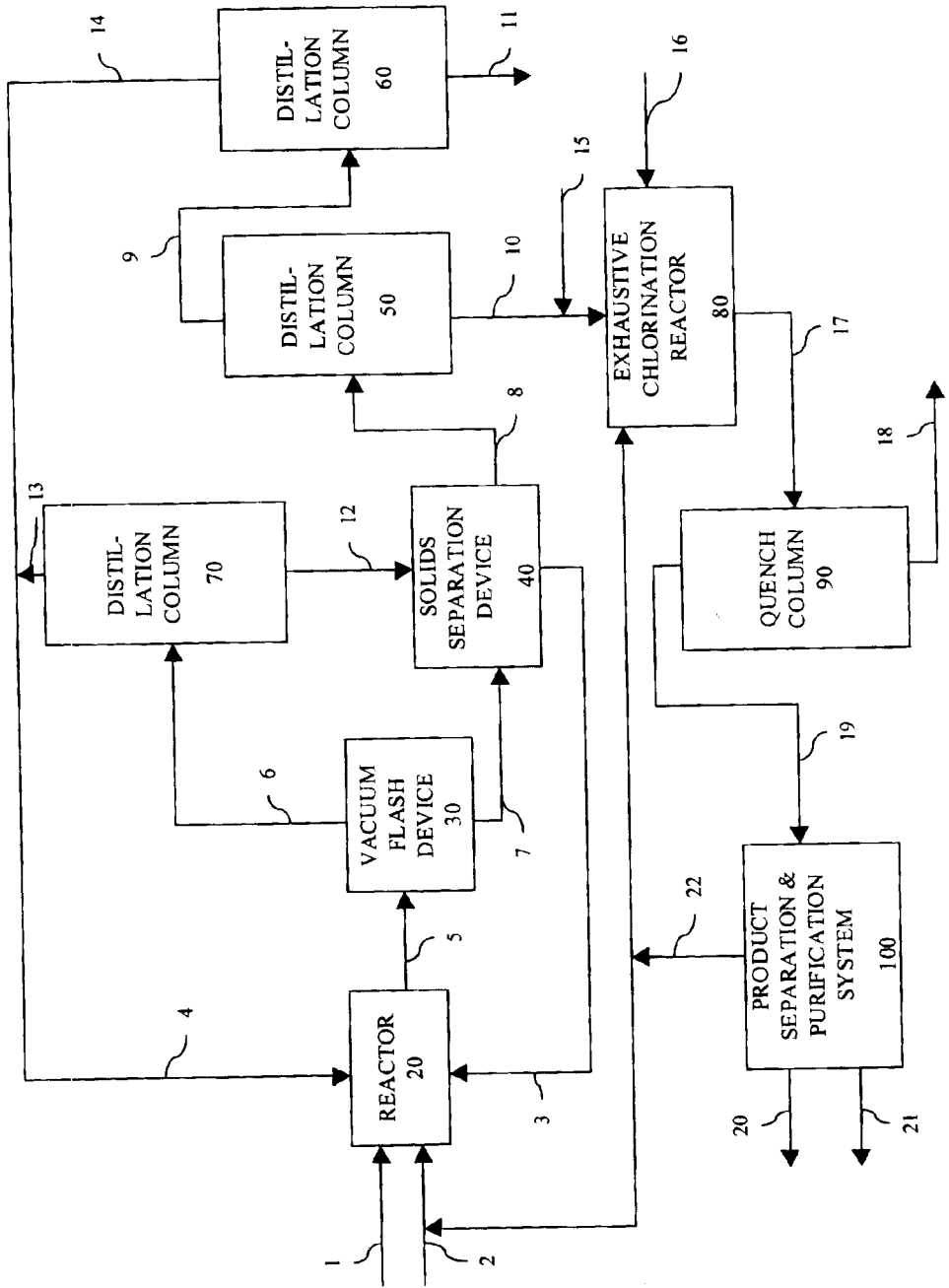

METHOD FOR REUSING HEAVY END BY-PRODUCTS IN THE MANUFACTURE OF POLYCHLORINATED ALKANES

FIELD OF INVENTION

The herein disclosed invention finds applicability in the field of haloalkane production.

BACKGROUND OF THE INVENTION

The formation of polychlorinated hydrocarbons containing three or more carbon atoms by the addition of a chlorinated alkane to an alkene is a process well documented in the art. For example, Wilson et al (U.S. Pat. No. 5,792,893) describe the manufacture of 1,1,1,3,3,3-hexachloropropane by the addition of carbon tetrachloride to 1,1-dichloroethene using a catalyst comprising copper and a solvent selected from a $C_3$ to a $C_5$ alkanenitrile. Wilson et al (U.S. Pat. No. 6,313,360) teach the manufacture of 1,1,1,3,3-pentachloropropane by the addition of carbon tetrachloride to vinyl chloride in the presence of a catalyst mixture comprising organophosphate solvent, iron metal and ferric chloride. These addition reactions in general are referred to as telomerization reactions.

While telomerization reactions can generally be made to proceed with high selectivity to the desired products, invariably some unwanted by-products are also produced. Sometimes an isomer of the desired polychlorinated alkane is formed. Heavy end by-products are usually present that result at least partially by the addition of the desired product with unreacted olefine feed still present in the reaction media. For example, in the production of 1,1,1,3,3,3-hexachloropropane by the addition of carbon tetrachloride to 1,1-dichloroethene, several percent 1,1,1,3,3,5,5,5-octachloropentane is also produced by the addition of the hexachloropropane to unreacted 1,1-dichloroethene. Similarly, in the production of 1,1,1,3,3-pentachloropropane by the addition of carbon tetrachloride to vinyl chloride, several percent 1,1,3,3,5,5- and 1,1,1,3,5,5-hexachloropentane are also formed. These compounds have higher boiling points than the desired products, and thus are typically removed from the process as heavy ends. Due to limitations in the distillation process, often some of the desired $C_3$ or higher polychlorinated alkane product may also be present in this heavy ends stream. Normally, these heavy ends would be disposed of as waste by incineration or other environmentally acceptable methods, and thus are an inefficiency in the utilization of the starting materials.

OBJECTS OF THE INVENTION

An object of the invention is to efficiently produce haloalkane products.

A further object is the conversion of waste halohydrocarbon by-products into useful reactants.

SUMMARY OF THE INVENTION

The reuse of heavy end by-products formed when manufacturing $C_3$ or higher polychlorinated alkanes via the catalytic addition of carbon tetrachloride to an olefine or chloroolefine is described. The improvement consists of (1) recovering the higher molecular weight heavy ends via distillation or other suitable means, (2) subjecting the recovered heavy ends to exhaustive high temperature chlorination, (3) recovering the carbon tetrachloride thus produced, and (4) recycling the carbon tetrachloride to produce additional desired $C_3$ or higher polychlorinated alkane. Since the aforementioned heavy end by-products are generally considered waste, this reduces the quantity of material for disposal and reduces the overall cost.

The process of the invention is directed to the recovery of the value from a substantial portion of the heavy ends and other undesired chlorohydrocarbons generated during the production of a $C_3$ or higher polychlorinated alkane. The $C_3$ or higher polychlorinated alkane is preferably produced by the addition reaction between carbon tetrachloride and an olefine or chloroolefine, though any known methods can be used to generate the desired product. A variety of catalysts or catalyst systems may be used to promote the addition reaction. The type of catalyst used does not impact the scope of this invention as long as it can be removed from the by-product streams. The by-products are removed from the desired $C_3$ or higher polychlorinated alkane via distillation or other appropriate means known to those skilled in the art. These by-products are then subjected to exhaustive chlorination in either the presence or absence of a catalyst to produce carbon tetrachloride and tetrachloroethene. Examples of such an exhaustive chlorination in the absence of a catalyst are given by Davis et al (U.S. Pat. No. 2,442,323), R. G. Heitz et al (U.S. Pat. No. 2,442,324), Warren (U.S. Pat. No. 2,577,388), Warren (U.S. Pat. No. 2,727,076), Obrecht (U.S. Pat. No. 2,857,438), or Petrosky (U.S. Pat. No. 5,426,256). The by-products can be chlorinated alone or, more preferably, in combination with other hydrocarbons or chlorohydrocarbons. More preferably, the by-product stream is blended with other $C_1$ to $C_3$ hydrocarbons or chlorohydrocarbons, which minimizes the formation of undesired hexachlorobutadiene and hexachlorobenzene in the exhaustive chlorination. The exhaustive chlorination process can be operated under conditions to maximize the amount of carbon tetrachloride produced. This carbon tetrachloride can then be returned as feed material to the original process to produce the $C_3$ or higher polychlorinated alkane. Alternatively, the carbon tetrachloride or tetrachloroethene can be sold directly as finished products.

More specifically, the invention is directed to a method for recovering much of the carbon and chlorine value in the heavy ends waste formed in the production of a $C_3$ or higher polychlorinated alkane via the catalytic addition of carbon tetrachloride to an olefine or a chlorinated olefine. The improvement comprises separating the heavy ends and any other low or high-boiling chlorohydrocarbon impurities from the desired product, then subjecting the separated heavy ends and impurities to a high temperature (500–700 degrees C.) exhaustive chlorination. The heavy ends and impurities may be chlorinated alone or mixed with other hydrocarbon or chlorinated hydrocarbon feed materials. The exhaustive chlorination is operated at conditions necessary to produce carbon tetrachloride, tetrachloroethene, and minor amounts of hexachlorobutadiene and hexachlorobenzene by-products. The chlorination process can be operated to maximize the amount of carbon tetrachloride produced. This carbon tetrachloride is then purified by distillation or other suitable means known in the art and returned to the telomerization process as feed material for further production of a $C_3$ or higher polychlorinated alkane. Alternatively, the carbon tetrachloride and/or tetrachloroethene produced in the chlorination process may be used in other suitable processes, or sold directly as a finished product.

Said another way, the herein disclosed invention is directed to an improved method for recovering much of the carbon and chlorine value from the heavy ends and from other undesired by-products formed during the production of a $C_3$ or higher polychlorinated alkane by the reaction of carbon tetrachloride and an olefine or chlorinated olefine. The inventive improvement comprises the step of first separating the heavy ends and any other higher or lower boiling chlorohydrocarbon impurities from most of the desired product, and subjecting the separated heavy ends and impurities therewith to a high temperature exhaustive chlorination process to produce carbon tetrachloride, tetrachloroethene, along with minor amounts of hexachlorobutadiene and hexachlorobenzene by-products. Exhaustive chlorination is conducted at a temperature between 500 and 700° C. and preferably at 600° C.; and with the pressure of from atmospheric to 100 psig with 30 psig being preferred. The method can be carried out wherein the production of the $C_3$ or higher polychlorinated alkane is by the catalytic addition of carbon tetrachloride to an olefine or a chlorinated olefine. In the process the olefine may be ethene and the chlorinated olefine may be a member of the group consisting of chloroethylene, dichloroethylene, trichloroethylene and tetrachloroethylene. In the high temperature exhaustive chlorination process to produce carbon tetrachloride, tetrachloroethene and minor amounts of hexachlorobutadiene and hexachlorobenzene by-products, the process can be either catalytic or non-catalytic. In the process the carbon tetrachloride can be purified by distillation and returned to the reactor. The heavy ends from the process to produce a $C_3$ or higher polychlorinated hydrocarbon may contain substantial amounts of the desired $C_3$ or higher polychlorinated hydrocarbon due to inefficiencies in the purification steps and may be subjected to high temperature exhaustive chlorination without further effort to remove the remainder of the desired $C_3$ or higher polychlorinated hydrocarbon. The heavy ends from the process may be subjected to the high temperature exhaustive chlorination alone, or mixed with other hydrocarbon or chlorohydrocarbon feed materials. Further, the heavy ends can be mixed with other $C_1$ to $C_3$ hydrocarbons or chlorohydrocarbons, to minimize the formation of unwanted by-products in the exhaustive chlorination step. Hydrocarbons or chlorinated hydrocarbons can be added to the heavy ends containing the undesired chloro-compounds. The exhaustive chlorination process can be maximized to produce carbon tetrachloride by running the process with a higher level of excess chlorine.

Exemplary of olefins and chlorinated olefines contemplated by the processes of this invention are ethylene, chloroethylene, dichloroethylene, trichloroethylene and tetrachloroethylene. While the invention has been defined mainly in terms of ethylene, other alkene derivatives would be operative.

DESCRIPTION OF THE INVENTION

One aspect of the invention is described with reference to FIG. 1, which illustrates a schematic diagram of the primary process steps of the inventive method for preparing 1,1,1,3,3,3,-hexachloropropane.

The reactants 1,1-dichloroethene and carbon tetrachloride are fed to telomerization reactor 20 through lines 1 and 2, respectively. In reactor 20, the reactants are contacted in the liquid phase in the presence of a copper chloride catalyst and $C_3$ to $C_5$ alkanenitrile solvent, to form 1,1,1,3,3,3-hexachloropropane and a small amount of 1,1,1,3,3,5,5,5-octachloropentane.

Reactor effluent 5 is fed to a vacuum flash vessel or column 30. The reactor effluent is then separated into at least two portions. The first portion comprises components having a boiling point lower than that of hexachloropropane, and the second portion comprises components having a boiling point greater than or equal to that of hexachloropropane. Overhead product 6 from the vacuum flash vessel or column 30 is fed to distillation column 70. Column 70 separates the 1,1-dichloroethene and carbon tetrachloride overhead as light ends 13 from the alkanenitrile solvent as bottoms 12. Light ends 13 from column 70 and light ends 14 from column 60 can be optionally recycled to the reactor.

The bottoms 7 from vacuum flash vessel or column 30, i.e., the second portion, consists of a liquid phase containing both hexachloropropane and octachloropentane, as well as a solids phase of fine copper chloride particles. The bottoms 7 can be cooled, and the solids removed therefrom by, e.g., sedimentation and/or filtration, using a settling vessel, filter, hydrocyclone, centrifuge or other suitable solids separation device 40. Preferably, the solids separation device is a settling vessel and a filter. After filling the settling vessel with bottoms 7, the solids are allowed to settle out. Then, the liquid is drawn off and filtered. Solvent can then be added to dissolve the copper chloride. Moreover, the recovered copper chloride in the settling vessel can be re-dissolved by the solvent, i.e., the $C_3$ to $C_5$ alkanenitrile, contained in the bottoms from the distillation column 70. This solvent and re-dissolved catalyst in line 3 can then be optionally recycled to reactor 20.

Subsequent to removal of the solids, liquid stream 8 can be fed to distillation column 50, where the lower boiling point compound(s), including hexachloropropane, are distilled overhead as line 9. The higher boiling compounds, primarily octachloropentane, are removed in bottoms 10.

The overhead product 9 from distillation column 50 can next be fed to distillation column 60, where remaining quantities of lower boiling compounds can be distilled overhead as line 14. These compounds can then be recycled to reactor 20. Purified hexachloropropane remains as bottoms product 11.

Stream 10, consisting primarily of octachloropentane and some hexachloropropane, is mixed with other $C_1$–$C_3$ hydrocarbon or chlorohydrocarbon feeds, such as 1,2-dichloropropane, 15. The mixed stream is fed to the exhaustive chlorination reactor 80 along with chlorine, 16. The product stream 17 is sent to a quench column 90. The bottoms stream 18, consisting primarily of hexachloroethane, hexachlorobutadiene, and hexachlorobenzene, can be either disposed of in an environmentally acceptable manner or partially recycled to the chlorination reactor 80. Overhead from quench column 90 is sent to a product separation and purification system. HCl and any unreacted chlorine are removed as stream 20. The chlorine can optionally be separated and returned to the chlorination reactor 80. Tetrachloroethene 21 is recovered as product or partially returned to the chlorination reactor 80 as reactive diluent. Carbon tetrachloride is removed as stream 22. A portion of stream 22 may be returned to the chlorination reactor 80 as reactive diluent. The remainder of stream 22 is returned to the telomerization reactor 20 as feed material.

Another aspect of the invention is described with reference to FIG. 2, which illustrates a schematic diagram of the primary process steps of the inventive method for preparing 1,1,1,3,3,3-pentachloropropane.

Tributyl phosphate (TBP), iron, vinyl chloride, and carbon tetrachloride are fed into a telomerization reactor 20 through lines 1 through 4, respectively. In reactor 20, the reactants and catalyst system are contacted in the liquid phase to form the desired 1,1,1,3,3-pentachloropropane and lesser amounts of 1,1,1,2,3-pentachloropropane, 1,1,3,3,5,5- and 1,1,1,3,5,5-hexachloropentane.

Reactor effluent 8 is fed to a vacuum flash/distillation system 30. The reactor effluent is then separated into at least three portions. The first portion comprises components having a boiling point equal to or lower than that of 1,1,1,3,3-pentachloropropane and consists primarily of vinyl chloride, carbon tetrachloride, 1,1,1,3,3-pentachloropropane, 1,1,1,2,3-pentachloropropane, and minor amounts of the two hexachloropentane isomers. This portion is fed as stream 9 to distillation column 40. Column 40 separates the vinyl chloride and carbon tetrachloride overhead as light ends 13 from the crude pentachloropropane as bottoms 14. Light ends 13 from column 40 can be recycled to reactor 20.

The bottoms 11 from the vacuum flash/distillation system 30, consists of a liquid phase containing iron, TBP, and small amounts of hexachloropentane isomers. The bottoms 11 can be recycled to telomerization reactor 20. A small portion of this stream can be purged as stream 12 and sent to a disposal process.

The third portion from the vacuum flash/distillation system 30 consists primarily of hexachloropentane isomers, plus smaller portions of both pentachloropropane isomers and other minor chlorinated hydrocarbon impurities. This stream is essentially free of iron or TBP. This is fed as stream 10 to the exhaustive chlorination reactor 60.

Bottoms from distillation column 40 contain the desired 1,1,1,3,3-pentachloropropane product plus minor amounts of 1,1,1,2,3-pentachloropropane and hexachloropentane isomers. This is fed as stream 14 to column distillation 50, where the desired product 1,1,1,3,3-pentachloropropane is removed overhead as 15. The higher boiling compounds, primarily 1,1,1,2,3-pentachloropropane and hexachloropentane isomers are removed in bottoms 16, which is also fed to the exhaustive chlorination reactor 60.

Streams 10 and/or 16, consisting primarily of hexachloropentane isomers and pentachloropropane isomers, are mixed with other $C_1$–$C_3$ hydrocarbon or chlorohydrocarbon feeds, such as 1,2-dichloropropane, 17. The mixed stream is fed to the exhaustive chlorination reactor 60 along with chlorine, 18. The product stream 19 is sent to a quench column 70. The bottoms stream 20, consisting primarily of hexachloroethane, hexachlorobutadiene, and hexachlorobenzene, can be either disposed of in an environmentally acceptable manner or partially recycled to the chlorination reactor 60. Overhead from quench column 70 is sent as stream 21 to a product separation and purification system, 80. HCl and any unreacted chlorine are removed as stream 22. The chlorine can optionally be separated and returned to the chlorination reactor 60. Tetrachloroethene 23 is recovered as product or partially returned to the chlorination reactor 60 as reactive diluent. Carbon tetrachloride is removed as stream 24. A portion of stream 24 may be returned to the chlorination reactor 60 as reactive diluent. The remainder of stream 24 is returned to the telomerization reactor 20 as feed material.

EXAMPLES

A laboratory-scale reactor was used in the following examples. The reactor was a 4-inch Inconel pipe fitted with a carbon liner, giving an internal volume of approximately 620 cubic centimeters. Chlorine from a 150-pound cylinder was metered through a glass rotameter and into the reactor nozzle. Carbon tetrachloride was used as a reactive diluent to help control the reaction temperature. Carbon tetrachloride diluent and the desired liquid feed composition were pre-mixed in a 1-gallon jug and pumped into the reactor nozzle where the liquid vaporized and mixed with the chlorine. The reaction was completed at 590 degrees C., 30 psig, and a vapor residence time of approximately 15 seconds. After reaction, the vapor effluent was condensed in a water-cooled receiver, from which liquid samples were taken for organic analysis by gas chromatography (GC) and mass spectrometry (GC/MS). The non-condensable gases passed through a vent line and back-pressure control valve, and to a caustic/water scrubber. Vent samples were taken immediately after the pressure control valve and titrated for chlorine and HCl.

The heavy ends introduced in Examples 2–4 were by-product material from a process in which 1,1,1,3,3,3-hexachloropropane was produced by the catalytic addition of carbon tetrachloride to 1,1-dichloroethene. These heavy ends contained 43 percent 1,1,1,3,3,3-hexachloropropane and 44 percent 1,1,1,3,3,5,5,5-octachloropentane. The heavy ends herein employed can be obtained by processes set forth in U.S. Pat. No. 5,792,893 to Wilson.

Example 1

Example 1 was a baseline run conducted using only propylene dichloride (1,2-dichloropropane or PDC) as the organic feed and carbon tetrachloride as the reactive diluent. Experimental results are shown in Table I. Net production of carbon tetrachloride and tetrachloroethene were 143.88 and 100.79 grams per hour, respectively, for a total of 244.67 grams per hour of desired products. Small amounts of hexachloroethane, hexachlorobutadiene, and hexachlorobenzene were also produced as normal by-products of the reaction. Hexachloroethane can be recycled to the reactor to be converted to desired tetrachloroethene product. Hexachlorobutadiene and hexachlorobenzene are normally considered wastes and must be disposed of by incineration or other environmentally acceptable practices. A total of 1.25 grams per hour of (hexachlorobutadiene+hexachlorobenzene) were produced in this example.

Example 2

In Example 2, approximately 4.9 wt % of the 1,2-dichloropropane feed was replaced with the heavy ends mixture described above. The same amount of carbon tetrachloride was used as the reactive diluent as in Example 1. Net carbon tetrachloride and tetrachloroethene production was 154.20 and 90.67 grams per hour, respectively, for a total of 244.87 grams per hour of desired products. A total of 1.38 grams per hour of (hexachlorobutadiene+hexachlorobenzene) were produced in this example.

Example 3

In example 3, approximately 14.3 weight percent of the 1,2-dichloropropane feed was replaced with the heavy ends mixture described above. Approximately the same amount of carbon tetrachloride was used as the reactive diluent as in Example 1. Net carbon tetrachloride and tetrachloroethene production were 157.75 and 73.80 grams per hour, respectively, for a total of 231.55 grams per hour of desired products. A total of 1.36 grams per hour of (hexachlorobutadiene+hexachlorobenzene) were produced in this example.

Example 4

In example 4, approximately 31.2 weight percent of the 1,2-dichloropropane feed was replaced with the heavy ends mixture described above. Approximately the same amount of carbon tetrachloride as before was used as the reactive diluent as in Example 1. The chlorine feed rate was increased relative to Examples 2 and 3 to illustrate one manner of increasing the production of carbon tetrachloride relative to tetrachloroethene. Net carbon tetrachloride and tetrachloroethene production was 165.20 and 57.34 grams per hour, respectively, for a total of 222.54 grams per hour of desired products. A total of 1.02 grams per hour of (hexachlorobutadiene+hexachlorobenzene) were produced in this example.

No unreacted 1,1,1,3,3,3-hexachloropropane or 1,1,1,3,3, 5,5,5-octachloropentane was detected in the condensed liquid product from any example to a detection level of 1 ppm by weight.

Obviously, many modifications may be made without departing from the basic spirit of the present invention. Accordingly, it will be appreciated by those skilled in the art that within the scope of the appended claims, the invention may be practiced other than has been specifically described herein.

TABLE I

|  | Example # | | | |
| --- | --- | --- | --- | --- |
|  | 1 | 2 | 3 | 4 |
| wt % heavy ends in PDC Feed | 0 | 4.9 | 14.3 | 31.2 |
| Feed Rates |  |  |  |  |
| Cl2 g/hr | 361.62 | 345.54 | 328.24 | 361.62 |
| PDC g/hr | 82.56 | 78.68 | 68.50 | 55.79 |
| CCl4 g/hr | 100.09 | 100.59 | 96.82 | 96.16 |
| Heavy ends g/hr | 0.00 | 4.05 | 11.40 | 25.27 |
| Total | 544.27 | 528.86 | 504.96 | 538.84 |
| Effluent |  |  |  |  |
| g/hr Cl2 | 30.71 | 29.48 | 31.05 | 84.10 |
| g/hr HCl | 165.12 | 149.70 | 140.52 | 131.21 |
| g/hr CCl4 | 243.98 | 254.79 | 254.57 | 261.35 |
| g/hr Tetrachloroethene | 100.79 | 90.67 | 73.80 | 57.34 |
| g/hr Hexachloroethane | 2.43 | 2.84 | 3.65 | 3.81 |
| g/hr Hexachlorobutadiene | 1.02 | 1.14 | 1.02 | 0.78 |
| g/hr Hexachlorobenzene | 0.23 | 0.24 | 0.34 | 0.25 |
| Total | 544.27 | 528.86 | 504.96 | 538.84 |
| Net g/hr CCl4 | 143.88 | 154.20 | 157.75 | 165.20 |
| Net g/hr Tetrachloroethene | 100.79 | 90.67 | 73.80 | 57.34 |
| g/hr (Hexachlorobutadiene + Hexachlorobenzene) | 1.25 | 1.38 | 1.36 | 1.02 |

What is claimed is:

1. A method for recovering much of the carbon and chlorine value from the heavy ends and other undesired by-products formed during the production of a $C_3$ or higher polychlorinated alkane by the reaction of carbon tetrachloride and an olefine or chlorinated olefine, the improvement comprising the step of first separating the heavy ends and any other higher or lower boiling chlorohydro-carbon impurities from most of the desired product, and subjecting the separated heavy ends and impurities therewith to a high temperature exhaustive chlorination process to produce carbon tetrachloride, tetrachloroethene, and minor amounts of hexachlorobutadiene and hexachlorobenzene by-products.

2. The method of claim 1 wherein the high temperature exhaustive chlorination is conducted between 500 and 700° C.

3. The method of claim 2 wherein the pressure during exhaustive chlorination is between atmospheric and 100 psig.

4. The method of claim 3 wherein the process during exhaustive chlorination is carried out at about 600° C. and at about 30 psig.

5. The method of claim 1 wherein the production of the $C_3$ or higher polychlorinated alkane is by the catalytic addition of carbon tetrachloride to an olefine or chlorinated olefine.

6. The method of claim 5 wherein the olefine is ethene.

7. The method of claim 5 wherein the chlorinated olefine is a member of the group consisting of chloroethylene, dichloroethylene, trichloroethylene and tetrachloroethylene and tetrachloroethylene.

8. The method of claim 1 wherein the high temperature exhaustive chlorination process to produce carbon tetrachloride and tetrachloroethene and minor amounts of hexachlorobutadiene and hexachlorobenzene by products is either catalytic or non-catalytic.

9. The method of claim 1 wherein the carbon tetrachloride is purified by distillation and returned to the reactor as feed material for further production of the desired $C_3$ or higher polychlorinated alkane.

10. The method of claim 1 wherein heavy ends from the process to produce a $C_3$ or higher polychlorinated hydrocarbon contains a substantial portion of the desired $C_3$ or higher polychlorinated hydrocarbon due to inefficiencies in the purification steps and is subjected to high temperature exhaustive chlorination without further effort to remove the remainder of the desired $C_3$ or higher polychlorinated hydrocarbon.

11. The method of claim 1 wherein the heavy ends from the process to produce a $C_3$ or higher polychlorinated hydrocarbon is subjected to the high temperature exhaustive chlorination alone, or mixed with other hydrocarbon or chlorohydrocarbon feed materials.

12. The method of claim 11 wherein the heavy ends are mixed with other $C_1$ to $C_3$ hydrocarbons or chlorohydrocarbons, to minimize the formation of unwanted by-products in the exhaustive chlorination step.

13. The method of claim 1 wherein other hydrocarbons or chlorinated hydrocarbons are added to the heavy ends containing the undesired chloro-compounds.

14. The process of claim 1 wherein the process is maximized to produce carbon tetrachloride.

15. The process of claim 1 wherein the carbon tetrachloride is further purified.

16. The process of claim 1 wherein the carbon tetrachloride is returned to the reactor to further react with the olefine or chlorinated olefine.

* * * * *

UNITED STATES PATENT AND TRADEMARK OFFICE
CERTIFICATE OF CORRECTION

PATENT NO.        : 7,112,709 B2
APPLICATION NO. : 10/657895
DATED             : September 26, 2006
INVENTOR(S)       : Rodney L. Klausmeyer Page 1 of 1

It is certified that error appears in the above-identified patent and that said Letters Patent is hereby corrected as shown below:

On The Title Page
Item (73) Assignee: Replace "Vulcan Chemicals, Birmingham, AL" with -- Occidental Chemical Corporation, Dallas, TX --

Item (74) Attorney, Agent, or Firm: Replace "Armstrong, Kratz, Quintos, Hanson & Brooks, LLP" with -- Fish & Richardson P.C. --

Figure 2:
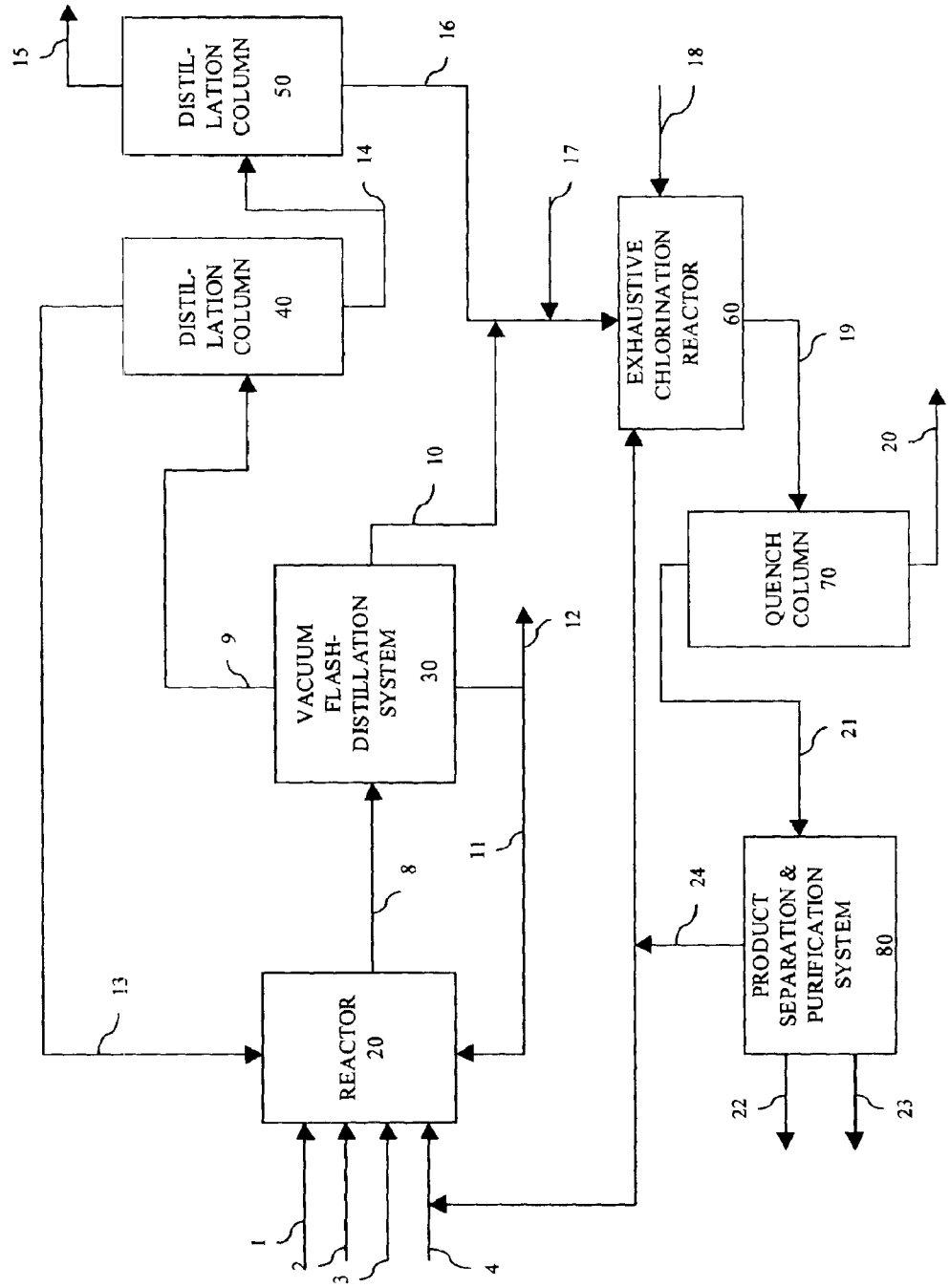

In column 3, line 51 – insert the following paragraph:
--      Brief Description of the Drawings
        Figure 1 and Figure 2 illustrate the primary process steps of the invention. --

In column 4, line 63 – replace "1,1,1,3,3,3-pentachloropropane" with -- 1,1,1,3,3-pentachloropropane --

Signed and Sealed this

Eleventh Day of December, 2007

JON W. DUDAS
*Director of the United States Patent and Trademark Office*